(12) United States Patent
Manderson

(10) Patent No.: US 6,488,685 B1
(45) Date of Patent: Dec. 3, 2002

(54) EXTRAMEDULLARY ROD FIXATEUR FOR BONES

(76) Inventor: Easton L. Manderson, 1750 Sir Galahad Way, Ashton, MD (US) 20861

( * ) Notice: Subject to any disclaimer, the term of this patent is extended or adjusted under 35 U.S.C. 154(b) by 0 days.

(21) Appl. No.: 09/343,180

(22) Filed: Jun. 30, 1999

Related U.S. Application Data

(63) Continuation-in-part of application No. 08/494,678, filed on Jun. 26, 1995, now abandoned.

(51) Int. Cl.7 .............................................. A61B 17/70
(52) U.S. Cl. ...................................................... 606/69
(58) Field of Search ............................ 606/60, 61, 63, 606/69, 72, 73

(56) References Cited

U.S. PATENT DOCUMENTS

| | | | | |
|---|---|---|---|---|
| 4,448,191 A | * | 5/1984 | Rodnyansky et al. | 606/61 |
| 4,454,876 A | * | 6/1984 | Mears | 606/69 |
| 5,087,259 A | * | 2/1992 | Krenkel | 606/60 |
| 5,147,361 A | * | 9/1992 | Ojima et al. | 606/69 |
| 5,197,966 A | * | 3/1993 | Sommerkamp | 606/69 |
| 5,681,311 A | * | 10/1997 | Foley et al. | 606/69 |
| 5,693,053 A | * | 12/1997 | Estes | 606/72 |

* cited by examiner

Primary Examiner—David J. Isabella
(74) Attorney, Agent, or Firm—Nigel L. Scott, Esquire

(57) ABSTRACT

Described is a fixateur consisting of a solid rod designed for bridging two portions of a broken long bone, united or ununited, and maintaining the divided portions of the bone in rigid alignment with each other.

The solid rod fixateur is designed to be rigidly attached to the damaged long bone by means of a pair of partly tubular plates at either end of the rod. These plates provide the sole means of attachment of the fixateur to the bone i.e there is has no provision for any attachments along, beside or through any portion of the rod that would allow it to be apposed to, or attached to any portion of the bone for which it is providing support for osteosynthesis. By its design and method of rigid attachment to the bone, through partly tubular end plates, the fixateur allows controlled motion at the fractured or non united portions of the bone fragments, a motion which stimulates rapidly forming external bridging callus formation for osteosynthesis of the long bone, a process that shortens the time of osteosynthesis of long bones so treated.

27 Claims, 5 Drawing Sheets

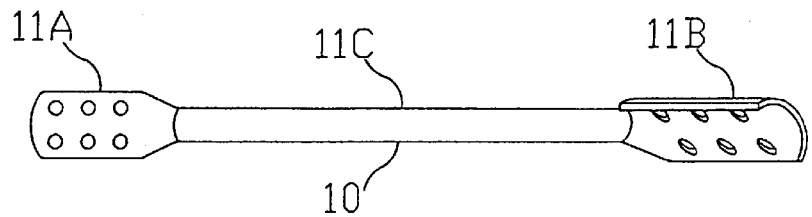
FIG. 1A
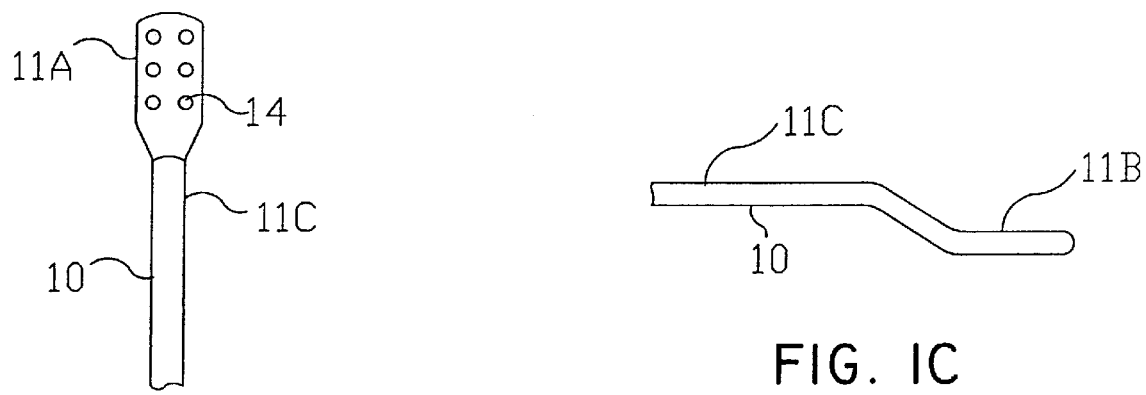
FIG. 1B
FIG. 1C
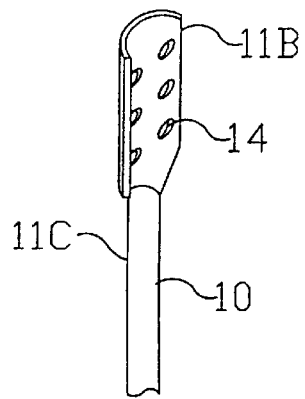
FIG. 1D

EXTRAMEDULLARY ROD FIXATEUR FOR BONES

CROSS REFERENCE TO RELATED APPLICATIONS

This application is a continuation-in-part of application Ser. No. 08/494,678 filed Jun. 26, 1995, now abandoned, for "Instrument for osteosynthesis of Long Bone Fractures—Manderson Sidebinder Implant."

EXTRAMEDULLARY ROD FIXATEUR FOR BONES

The present invention generally relates to a device to be used for internal fixation of bone fragments to effect osteosynthesis of ununited bone fragments. The fixateur is particularly suitable for fractures of long bones although it may be adaptable to bridge joints of long bones requiring arthrodesis or bones in a state of non union, malunion or pseudoarthrosis.

BACKGROUND OF THE INVENTION

It is well known in the art of bone fixation that the repair of fractured bones may be accomplished by the attachment of bone plates and intramedullary nails or rods to the injured bone to hold the fractured bone ends in place during healing. Bone Plates and intramedullary rods or nails are designed to provide rigid fixation and support for applied loads while being subjected to cyclical loads in tension, compression, torsion and or bending.

Bone plates are generally described as devices with at least one flattened surface and with holes or grooves for screws and wires, respectively, situated in or along the main body of the plate, to allow fixation of the flattened surface of the device to the bone surface by means of screws or wires for the purpose of holding the bone in place and achieve union of the bone fragments.

The bone plates traditionally are rigidly fixed to the bone to prevent motion between the fragments. Empirically bone union occurs with rigid fixation, but rigid fixation of the bone fragments along significant lengths and breaths of the bone will weaken the bone through stress shielding and disuse atrophy. The adverse effects of stress sheilding and disuse atrophy are prolonged healing time and refracture or discontinuity of the bone if the device is removed after osteosynthesis.

Other adverse effects of plates are as follows: Healing also is generally without the formation and protective function of external callus; applying the plate for rigid fixation requires surgical dissection of the non-osseous tissues, a process which injures the external vascular and nutritional sources of the bone fragments and which may be imprudent in the presence of preceding traumatic injury to the bone and non osseous tissue.

Screw holes of plates are weak points or stress risers that may cause failure or breakage of the plate during load application especially if this load application is repetitive or cyclical. If a plate does not have fixation applied throughout its entire length, fixation may be inadequate for load support during load application which is usually in several planes, a situation that may result in loss of axial and rotational alignment, malunion or nonunion of the fragments and or failure of the device along the stress rising non utilized screw holes. Needless to say, if several screw holes are left unused then the remaining portion of the plate is usually not rigid enough to withstand cyclical applied loads without failure or deformation.

Generally, the loading configuration to which an implant is subjected is not limited to one particular plane. There may be simultaneous forces in several planes. If this is the case, cross sections which are asymmetrical may not be as satisfactory as those which are symmetrical for load bearing purposes. Thus, a plate which is usually flattened on one or more surfaces will not bear loads equally in all directions and may be adequate to withstand forces in one direction but inadequate to withstand forces in another. By comparison a round section device has equal properties for load distribution and bearing in all directions.

Intramedullary nails or rods are commonly used to support long bone fragments to effect osteosynthesis. The rod has several advantages over the plate. Placement can be subcutaneous at an entry point to the intramedullary canal of the long bone thereby avoiding surgical injury to the extra osseous tissues that provide nutritional and vascular support to the bone fragments especially in times of injury thereby lessening the risk of infection. Unlike plates, they share functional loading in weight bearing during and after the osteosynthesis process thereby preventing disuse atrophy as seen with plate fixation for osteosynthesis. This feature makes a second operation for removal to allow functional load distribution to the bone often unnecessary. If removal is necessary, refracture of the bone is uncommon, unlike the case with removal of plates, because the functional capacity for load bearing returns to the bone during and after healing and before removal, since the rod shares function with the bone to which it is applied, thereby avoiding stress shielding of the bone.

For intramedullary osteosynthesis of long bones, the rod or nail may be rigid, flexible, circular, diamond shaped, rectangular, of open section or closed section. However, it has been proven that for a given cross sectional area, a closed circular configuration with symmetry in all directions is most reliable in sustaining forces applied in several planes.

The intramedullary rod or nail conventionally applied, has several disadvantages. Insertion technique has a steep learning curve and can be technically demanding and requires expensive and sophisticated equipment and well trained support personnel. Positioning of the patient must be precise to allow proper insertion and this is not always possible or practical for a seriously multiple injured or obese patient. The use of the intramedullary rod or nail is limited, almost precisely to treating the diaphyseal section of the long bone needing osteosynthesis.

Although axial alignment is usually assured with intramedullary rods or nails, rotational alignment is not assured unless the rod has a fluted end or unless the rod is locked proximally or distally with screws, a procedure that is difficult to do in the distal locking area. Because of the great difficulty in achieving precise screw placement, this step usually prolongs the operative time and time of exposure to radiation, consequently, intramedullary rodding or, nailing must be performed using fluoroscopy, to ensure precise placement.

SUMMARY OF THE INVENTION

In general, application of a strong, rigid rod for intramedullary placement for osteosynthesis of a long bone requires intramedullary reaming, a process that entirely destroys the inner ⅔ of the intramedullary vascular circulation to the diaphysis of the long bone. The outer ⅓ of the diaphysis is supplied by the external non osseous tissue. If this is also disrupted by injury at the time of reaming for nail or rod insertion then the undesirable situation of the diaphysis being completely without vascular supply exists making the bone fragments more susceptible to infection or the chances of union more unlikely.

If the rod is placed without reaming then the constraints of the intramedullary canal limits the diameter size of the rod or nail, a situation that may make it too thin and flexible for effective load bearing or support such as seen in cyclical weight bearing.

Moreover, after reduction of the fragments, the osteosynthetic device must be rigid enough to hold the fragments in the restored position and alignment during load application especially for the long bones of the lower extremity engaged in the cyclical load bearing of walking and for the long bones of the upper extremity engaged in cyclical load support as seen in crutch walking, for example.

The designer should make the device sufficiently rigid so as to provide no more than the maximal tolerable amount of relative motion during the healing process. Controlled motion at the non-united ends of the long bones is desirable to stimulate callus formation. The implant should also be rigid enough to withstand load sharing forces in all planes (compression, bending, twisting and tension), but not so rigid as to force the implant to continuously carry the load after healing has taken place since this situation would lead to fatigue failure of the implant. On the other hand, too much motion from a pliable or flexible rod could lead to a hypertrophic non-union in a long bone.

Considering the variation in anatomy and the biologic constraints on size of the device, the ideal osteosynthetic implant is difficult to select by material selection criteria only. However, in selecting an ideal device attention must be paid to factors including the combination of design, application, material selection, selection of cross sectional areas and lengths in broad categories such as small, medium and large. The device should meet ideals of minimal soft tissue damage during application, rapid application with very limited amount and use of sophisticated equipment and personnel, load sharing with the bone fragments to which the device is applied, before and after osteosynthesis. In addition, the device will provide support for the rapid development of external callus driven by the stimulus of load sharing that causes controlled, benign motion at the ununited bone ends; rigidity and rigid fixation away from the bone ends that will allow controlled motion at the ununited bone ends while at the same time allowing load bearing and support, even of a cyclical nature. Further, the invention describes an implant for osteosynthesis that will initially bear the total load of the injured biologic structure, since the initial and basic purpose of this device, should be to provide a means of load transmission across fractures or ununited bone fragments before synthesis has been achieved.

In accordance with applicant's invention, it is possible to overcome the many defects attributable to intramedullary rodding and extramedullary bone plate fixation through the use of an extramedullary rod which is capable of being rigidly attached to the extremities of a long bone, provide weight bearing support to the bone along its longtudinal axis and permit stimulatory forces of motion that generate callus repair at the point of nonunion of the bone. An entramedullary rod of this type is unknown to those skilled in the art.

OBJECTIVES OF THE INVENTION

A principal object of this invention is to provide rigid fixation of the bone fragments that will maintain axial and rotational alignment during load bearing of osteosynthesis.

Another object of this invention is to provide a bone fixateur that is preshaped to accommodate the general anatomy of the bone fragments to which it is applied and restore normal or near normal axial and rotational alignment of the bone after union.

Yet another object of the invention is to allow functional load sharing throughout the fixation before osteosynthesis and after osteosynthesis.

A further other object of the invention is for the device to be applied in a rigid manner to the bone fragments with minimal surgical damage to the soft tissues that are external and internal to the bone.

One more object of the invention is for it to be applied with little or no contact of the rod section to the bone fragments while still providing rigid support to the fragments for load bearing.

A final object of the invention is by design and application to provide a method that would allow beneficial motion at the ununited bone ends of long bones that will stimulate the formation of external bridging callus between the ununited bone ends.

BRIEF DESCRIPTION OF THE DRAWINGS

FIG. 1(A) is an enlarged perspective view of the implant of the present invention for use on the femur, tibia and fibia showing the rod section, directionally opposed partly tubular end plates, and screw holes.

FIG. 1(B) is an enlarged anterior/ posterior view of a partially tubular plate and rod and the confluent junction of the plate and rod.

FIG. 1(C) is an enlarged longitudinal cross-sectional view of the end plate of the implant showing the end plate and the rod section lying in different planes with respect to each other at their confluent junction.

FIG. 1(D) is an enlarged lateral cross-sectional view of the implant across the partly tubular plate showing the substantially flat outer surface, the concave inner surface of the implant and the pedicles on the plate.

DETAILED DESCRIPTION OF THE INVENTION

Figure 2A:
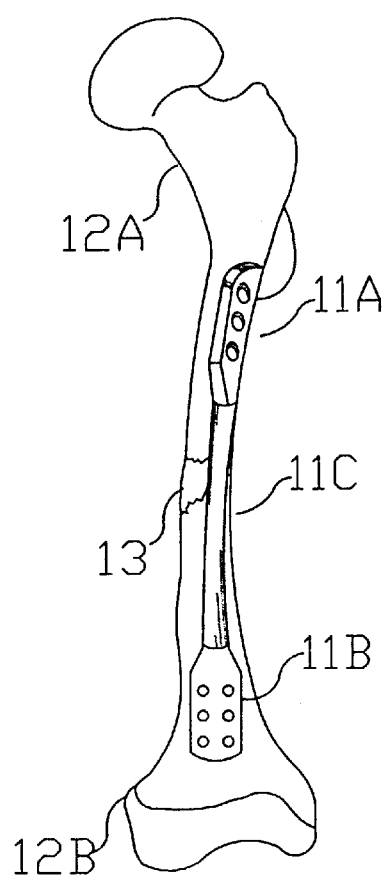
FIGS. 2(A) and 2(B) show the invention as applied to an instrument adapted for use on the femur showing a rod section connected to partially tubular end sections, with screw holes. The instrument is rigidily attached to the undamaged bone ends at a distance from the point of fracture.
Figure 2B:
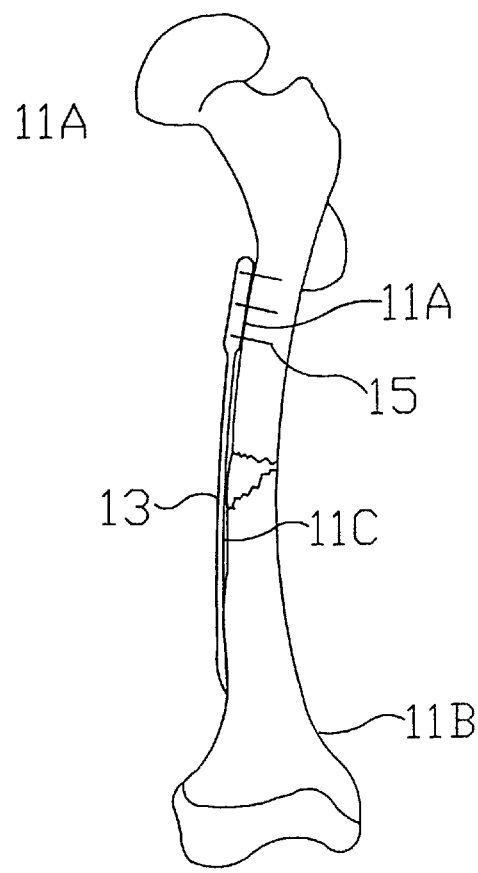
Figure 2C:
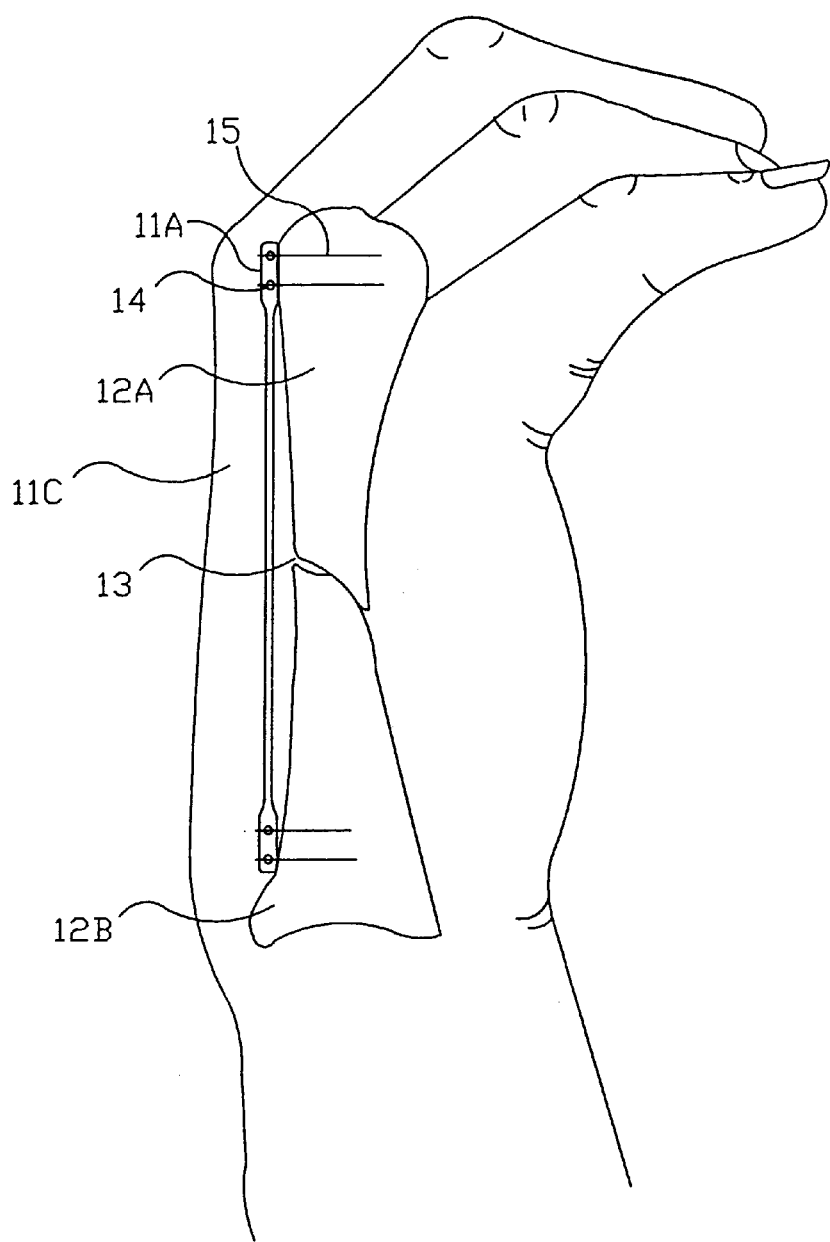
FIG. 2(C) shows the implant instrument in position for the repair of a phalangeal bone.
Figure 2D:
Figure 3A:
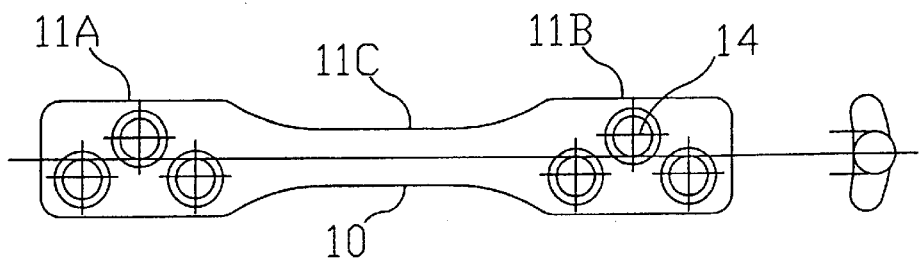
FIGS. 3A, 3B and 3C show forms of the device used in the repair of fractures of the ulnar, radial and wrist, respectively.
Figure 3B:
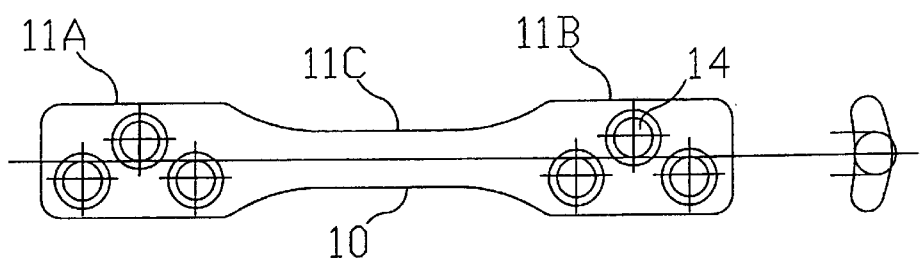
Figure 3C:
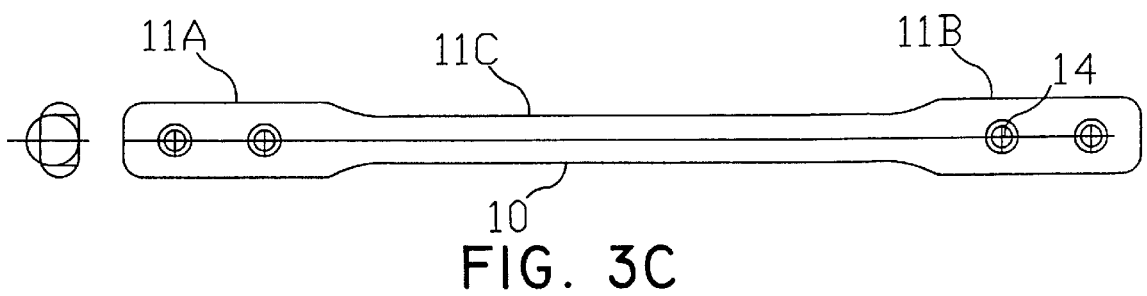
Figure 4A:
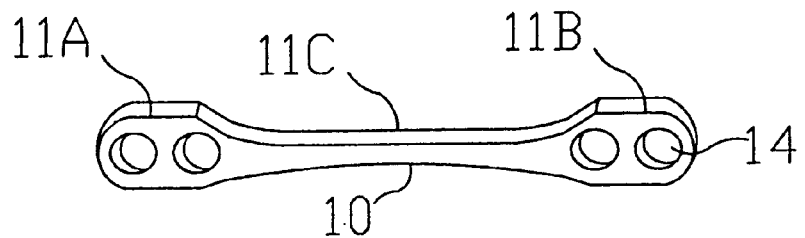
FIGS. 4A, 4B, and 4C are different sizes of the device for use on the phalangeal bones.
Figure 4B:
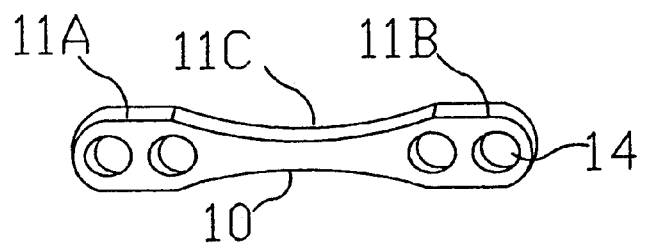
Figure 4C:
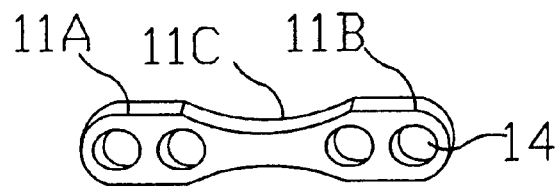

Referring to FIG. 1A there is shown a device having the numeral 10 made of a rigid inert material, such as stainless steel. The device 10 includes two identical substantially slot partially tubular plates end 11A and 11B with screw holes 14; and a middle rod section 11C which joins the end plates, 11A and 11B. FIG. 2A shows the implant in place on a fractured femur 12, it will be noted that the middle rod section, 11C of the device spans the ununited bone fragments 13, of the femur 12 and the partially tubular ends of the device are attached to the distal and proximal sections of the injured bone 12A and 12B by means of screws 15.

Referring specifically to FIG. 2A it can be seen that in practice the implant 10 is held in place on the fractured bone only at the extremities of the bone and that the implant is completely unattached to the fractured bone except by means of tubular end plates which are attached to the proximal and distal ends of the injured bone. Generally, however, each tubular end plate is designed to accommodate up to five screw holes 14. The rod 11, portion of the implant spans the fractured area so that no screws or fixation devices are close to the fracture zone. This spanning feature, in turn, allows rigid fixation of the instrument at the ends while leaving the central portion of the bone unaffected by the preserve of the instrument. This unique method of fixedly attaching the instrument to the extremities of the bone, only generates micromotion at the ununited bone ends that encourages and sustains the more rapid healing due to external bridging callus formation, rather than the healing by the slower primary bone healing seen with rigid fixation. Since no dissection is done in the fractured area, and since the device is fitted extramedullarily, there is no disturbance of the endosteal blood supply (inner $2/3$ of the cortex) or the periosteal blood supply (outer $1/3$ of the cortex).

As shown below, the device of this invention, 10 is designed in form and manner to fit on any of the long bones of the body, including the thigh, leg, arm, forearm and wrist bones. Each device will have a minor adjustment in form, shape or length to make it adaptable for the particular bone and the injured person.

The femoral "sidebinder," for fractures of the femur (thigh) will vary on either the left or the right and may vary in lengths from approximately 10 inches to 12 inches.

Tibial "sidebinder" with respect to the treatment of fractures of the tibia, the (leg) is approximately 10 inches to 11 inches and is also adaptable left or right handed applications.

The Humeral "sidebinder," for fractures of the humerus (arm) comes in two lengths, one approximately 9 inches and 10 inches, and is adaptable to left and right.

(forearm) the Radial "sidebinder," for fractures of the radius and (Forearm) ulnar "sidebinder," for fractures of the ulnar are one size, only and the length is determined accordingly.

Wrist spanner (for fractures of the wrist), this instrument is one size only and has four holes, two in each tubular end plate.

The instrument is designed to be implanted quickly and with minimum disturbance of the surrounding bone and tissue to facilitate early bone healing. Moving the plate sections away from the fracture line, as this implant does, decreases the rigidity of the plate fixation and allows for the maintenance of a stable but flexible environment in the region of the fracture. The flexibility also allows bending stress to be transmitted to the bone thereby preventing stress shielding. Further, because there are no stress rising holes in the spanning rod section, these implants can withstand cyclic loading such as crutchwalking for the humerus and weight bearing for the femur and tibia, without the need for additional external fixtures.

According to the procedure of this invention, the processes and techniques of intramedullary rod fixation are incorporated with those employed in extramedullary plate fixation to achieve results which have not been achieved previously.

In its preferred embodiment the implant which is used for the treatment of a femoral shaft fracture is designed to treat femoral shaft fractures. The device is designed with anterior and lateral curves and its length will coincide with the length of the femur being repaired. The essential modifier in length selection is the length needed to span the fracture and injury site since surgical plate application should be well away from the fracture zone. The cylindrical section of the device may vary in diameter from 10 to 12 millimeters to correspond to the size and weight of the injured person.

The length of the nail selected for fixation of the device to the non-fracture bone ends may be modified according to patient size (length of femur), patient age (presence of growth plate), fracture grade (extent of comminution) and fracture pattern (transverse, oblique, spiral). Fixation may be accomplished by means of screws, nails or wire. If screws are used the type of screw may vary in length, diameter or screw type depending on the nature of the fracture, the advantages to be gained by using one type of screw over another and the overall needs of he patient. In general, the diameter of the screws may be selected from among the following: 2.7, 3.5, 4.5, 6.5, 7.0 millimeters.

Considering these factors the appropriate length of the implant can thus be selected by aligning the non-sterile implant on the injured extremity during restoration of femur length under fluoroscopy, on the non injured thigh before reduction or along radiographs of the injured or non injured femur.

In order to insert the instrument on a fractured bone, place patient supine on the fracture table using fluoroscopy to restore anatomic length to the injured femur, two lateral incisions, one distal and one proximal to the fracture zone are made in the outer skin in the injured femur. The incision is connected by means of a submuscular tunnel through which the implant is inserted with the curve anterior. Fix the plate sections to the lateral cortices temporarily by placing Steinmann pins through a plate hole in the distal and proximal end plates. To fix the plate permanently to the bone, it is recommended to place at least three screws in each plate section, depending upon the length of the fractured bone, i.e. the injured bone (radius, femur) and the size of the tubular plate.

For supracondylar fractures 6.5 cancellous screws can be used in the distal metaphyseal fragment. If the bone is osteoporotic the fixation can be augmented with bone cement. Proper rotation of the bone will usually be ensured with identical lateral placement of the plate sections. The wounds should be copiously irrigated with antibiotic solution and closed in layers in the usual fashion. Closed suction drainage is optional if proper hemostasis has been achieved. Apply sterile dressing and discontinue traction, if used preoperatively.

Postoperatively, the patient may sit up in chair or get out of bed as general condition allows. Continue appropriate broad spectrum antibiotics started preoperatively and continue for 24–48 hrs, postoperatively. Physical therapy is indicated for upper and lower extremity strengthening and ambulation training is begun as soon as general condition allows with partial weight bearing for the affected extremity until bridging mature callus formation is seen radiographically, then full weight bearing is recommended.

Removal of the implant is optional. If removed, as per clinical situation or surgeon's choice after mature healing, the extremity should be protected with partial weight bearing and crutches or other walking aid for a period of at least six weeks.

The cylindrical rod fixateur is attached to the bone segments by plates at its ends rather than its sides and offset in such a manner that would allow it to provide little or no contact with any bone surface along which it traverses.

Each plate would contain at least 2 holes for 2 screws of appropriate sizes for small long bones and between 3 and 5 screw holes for fixation to large long bones of the extremities of appropriate sizes for long bones such as the humerus in the upper extremity and the tibia and femur in the lower unit extremity.

For long bones such as the humerus in the upper extremity and the tibia in the lower extremity, a predesigned built-in 90° rotation of the rod would be available to allow the plate sections to be attached to the proximal lateral metaphyseal areas, proximally, and the distal anterior, metaphyseal areas distally, simultaneously, which after length is restored by reduction techniques will assure restoration of correct rotational alignment.

On account of the 90° rotation of the rod used for stabilisation of the humerus or the tibia, the partially tubular plates are directional opposed to each other, so that when the plates are attached to the injured bone the natural alignment and rotational function of the bone is restored.

The rod may be made of suitable naturally occurring or man made material, including stainless steel, titanium or other presently known or unknown materials to be implanted in biological tissues of animals such as humans. If the rod is made of certified stainless steel or other such suitable material, and designed for an upper extremity long bone such as the humerus, and for lower extremity long bones such as the femur and tibia, an implant of appropriate rigidity and thickness must be selected. An internal rod fixateur for use on the long bones such as the humerus, femur, tibia should be designed to allow cyclical weight bearing of up to ½ the body weight immediately after application in order to allow controlled motion at the fracture site or united ends of the bone, to stimulate the formation of external bridging callus and up to full body weight once radiographs reveal external bridging callus.

This controlled motion at the site of the fracture or nonunion is effected by attaching the rigid rod subcutaneously through the attached plate sections only, to the bone fragments at or near the metaphyseal areas of the long bone fragments, away from the injured soft or bone tissues or areas of non-union of the bone fragments and encouraging loading of the bone fragments by weight bearing or active motion of the involved extremity. This is in direct contrast to conventional application of plates through direct approach to the injured bone area and soft tissue with application of the plate along a flat or contoured surface directly to the bone surface in and around the area of the fracture or nonunion and beyond the area of the fracture or non-union, a process that injuries the soft tissue and shields the bone from loading forces, thereby causing bone atrophy while preventing bridging, external callus formation.

Although those skilled in the art of osteosynthesis can appreciate that at times incising the skin in the area of the fracture or non-union, is necessary to clean or debride unwanted tissue the design and intent of application of this implantable fixateur is to apply it in such a way that its application will do little or no harm to the bone or non-osseous tissue in the region needing care and osteosynthesis; to apply it in such a manner that it will allow the natural physiologic healing process of callus formation and bridging of the bone fragments to be stimulated and enhanced; to apply it in such a manner that it will allow cyclical weight bearing of the extremity in which it is placed without permitting loss of the fixation, deformity of the bone fragments or failure of the implant through breaking, buckling or bending The design and application therefore, are integral features of a system designed to promote healing by peripheral callus formation.

Therefore to accomplish the above the rod fixateur is inserted subcutaneously atraumatically through an incision that is proximal or distal to the area of injury or non-union, harvested through an incision that is proximal or distal to the area of injury or non-union after passing atraumatically across the area of injury or non-union and rigidly fixed to or near the vascular and healthy metaphyseal areas of the long bone fragments.

Because the rod section of the fixateur which is continuous with the partly tubular plates is offset from the plate to lie in a different plane that is superior to the plane of the plate relative to the bone fragments, the rod lies away from the surface of the bone fragments to which the plates are attached, is not affixed to the bone surface or non osseous tissue, and because of its offset posture relative to the plate has little or no contact with the bone, a desirable feature that prevents contact injury to osseous or non osseous tissue and prevents disuse atrophy of the bone while providing support of the bone fragments and stimulation for callus formation.

The design of the end plates is critical to the function of the instrument. On its outer surface, that is the surface removed from attachment to the bone, the instrument is generally flat. On the other hand, the inside surface for attachment to the bone has a distinctive curvature to concide with the generally curved surface of the bone to which it is to be attached. In addition, the inside surface of the instrument has pedicles to facilitate the rigid non-continous attachment of the tubular plates to the bone. In addition, since the rod section of the implant has no protruding plate or other means of fixedly attaching the rod section to the bone, the rigidity of the attachment of the ends of the instrument to the bone is very important to the functioning of the device.

The foregoing is illustrative of the broad uses of the invention, however, it is not intended that all possible variations of the invention known to those skilled in the art have been included in this description.

What I claim is:

1. An extramedullary implant instrument for stabilization of fractured long bones consisting of a solid, elongated rod having identical substantially flat, partly tubular plates at each end of said rod, said implant being designed for rigid attachment to the nonfracture end of the bone by means of said partly tubular plates to permit said rod to provide longtudinal support to said fractured bone along the longtudinal axis of said bone, thereby maintaining the ununited bone fragments of said fractured bone in constant alignment with each other to effect osteosynthesis of said bones, said partly tubular plate on the ends of said implant being the sole means of fixed attachment of said implant to said fractured bone such that said rod section of said implant and said fractured bone are not fixedly attached to each other, said partly tubular plates each having at least two screw receiving holes therein, said partly tubular plates being generally rectangular in shape and having a wider cross-sectional diameter than the cross-sectional diameter of said rod section, said partly tubular plates having a generally flat outer surface and a generally concave inner surface to substantially conform to the surface curvature of said fractured bone, said partly tubular plates and said rod generally lying in different planes with respect to each other, the rod lying in a plane superior to said tubular plates, said partly tubular plates having a pre-determined angular setting in relation to each other and to said rod said angular setting being in conformity with the pre-fracture contour of the long bone to which said implant is to be attached, said implant, including said partly tubular plates and said rod section having a total length that is appropriate, after attachment, for restoration of the pre-fracture length of the particular long bone to which said instrument is to be attached, said implant, when fixedly attached to said fractured bone fragments by means of said partly tubular plates restores said fractured bone to its approximate pre-fracture length and contour, places said cylindrical rod section in parallel, contiguous and non-fixed alignment with said fractured bone and provides bearing support for said fractured bone during and after osteosynthesis.

2. An implant as claimed in claim 1 wherein said rod has a substantially uniform cross section continuous over the length thereof and lacks means for attachment to the bone or tissues.

3. An implant as claimed in claim 1 wherein said uniform cross-section is selected from the group consisting of an open section, rectangular, semicircular or diamond shaped.

4. An implant as claimed in claim 1 wherein said partly tubular plates have no more than 5 fastener receiving holes therein.

5. A solid, elongated cylindrical rod implant for osteosynthesis of ununited bone fragments as claimed in claim 1 having partly tubular plates at the ends thereof wherein said rod is offset in a superior plane to each of said plates so that upon attachment of said implant to said fractured bone said rod and said bone lie in separate planes and said bone and said partly tubular plates attached lie in the same plane.

6. An implant as claimed in claim 5 wherein said rod section is completely circular throughout the length thereof.

7. An implant as claimed in claim 5 wherein said rod section thereof is confluent with said partly tubular plates and have no stress risers at their points of confluence.

8. An implant as claimed in claim 5 wherein said partly tubular plates include fastener receiving openings for attachment of said implant to said fractured bone and wherein said fastener receiving openings include openings for accepting fastening devices ranging from of 2.5 millimeters to 7.0 millimeters.

9. An implant as claimed in claim 5 wherein said partly tubular plates have a substantially flat outer surface and includes no more than five fastener receiving openings for insertion of fastening devices to fixedly attach said partly tubular plates to said fractured bone and wherein the inner surface of said partly tubular plates is concave in shape and includes longitudinal pedicles thereon to limit the points of contact between said partly tubular plates and said fractured bone said partly tubular plates having a pre-determined angular setting in relation to each other and to said rod said angular setting being in conformity with the pre-fracture contour of the long bone to which said implant is to be attached.

10. An implant as claimed in claim 5 wherein the diameter of said rod is that diameter which is appropriate for the fractured long bone and wherein said rod will allow cyclical loading or weight bearing on said fractured long bone of no less than one half of the body weight of the injured person and wherein the overall length and diameter of said implant is determined according to the preferences and desires of the practitioner of the art of fixation, the long bone involved and according to the dictates of preoperative radiographs and clinical measurements of said fractured bone.

11. An implant as claimed in claim 5 for subcutaneous insertion in the area of the injury and rigid fixation at the metaphyseal areas distal from the fracture or ununited bone ends.

12. An implant as claimed in claim 5 wherein said rod is offset in a superior plane to said partly tubular plates and wherein said partly tubular plates have a pre-determined angular setting in relation to said rod said angular setting being in conformity with the pre-fracture contour of the long bone to which said implant is to be attached.

13. An implant as claimed in claim 5 wherein said rod when affixed to said fractured bone lies in parallel and contiguous alignment with said fractured bone and wherein said alignment between said rod and said bone results in the restoration of said fractured bone to its prefracture length and contour.

14. An implant as claimed in claim 5 wherein said implant has a in built 90 degree rotation along its longitudinal axis to facilitate placement of the partly tubular plate sections on the metaphyses of the extremities of the femur, humerus and tibia to restore the rotational alignment in said bones so as to restore them to their prefracture condition.

15. An implant as claimed in claim 1 wherein said implant when attached to the bone fragments by means of said partly tubular plates at the diaphysis of the ununited bone fragments assures correct axial rotation of said bone fragments with respect to each other.

16. An implant as claimed in claim 1 wherein said implant when attached to the bone fragments by means of said partly tubular plates at the diaphysis of the ununited bone fragments maintain axial alignment of said bone fragments.

17. An implant as claimed in claim 1 wherein said implant when attached to the bone fragments by means of said partly tubular plates at the diaphysis of the ununited bone fragments allows cyclical body weight-bearing and loading to the extremity without loss of alignment.

18. An implant as claimed in claim 1 wherein said implant when attached to said bone fragments by means of said partly tubular plates will allow controlled motion at the fracture site or ununited bone ends that will stimulate external callus bone formation.

19. An implant as claimed in claim 1 that is rigid and preshaped so that upon attachment to said fractured bone functional alignment is restored to said ununited bone fragments.

20. An implant as claimed in claim 1 wherein said implant is made out of a material selected from among the group of materials including stainless steel, titanium or other naturally occurring or man made materials.

21. An implant as claimed in claim 1 wherein said tubular plates adjoins the rod at the ends of the rod only and wherein said rod has no means for lateral attachment, fixation or apposition between said fractured bone and said rod.

22. An implant as claimed in claim 1 wherein the means for attachment of said partly tubular plates to said fractured bone includes screws, wires, cables or other fixation means.

23. An implant as claimed in claim 1 including partly tubular bone plates that is designed to be placed extramedullarly to the bone thereby requiring no reaming for placement.

24. An implant as claimed in claim 1 that may be inserted and applied to said fractured bone of with plain radiographic imaging equipment only and without the use fluoroscopy if so chosen by the practitioner of the art of fixation.

25. An extramedullary implant for stabilization of fractured long bones, placing and holding the ununited ends of said bones in fixed and constant alignment, and promoting the process of osteosynthesis and reunion of said fractured long bone consisting of a solid cylindrical rod having a pair of substantially flat, partly tubular fixation plates at each end of said rod, said fixation plates having fastener receiving openings for fastening said implant to the extremities of said fractured long bone, said substantially flat fixation plates having a concave inner surface for attachment of said plate to the curved surface of said fractured bones, said cylindrical rod being contoured to the shape and length of the particular bone to which it is to be attached, said substantially flat fixation plates and said cylindrical rod lying in different planes with respect to each other so that upon fixation of said tubular plates to said fractured bone said cylindrical rod is placed in parallel, non-contact alignment with the fractured long bone to which it is attached and provides weight bearing support for said fractured long bone along the longtudinal axis thereof, said implant being of such length as determined according to the pre-fracture length of said long bone to which it is to be attached so that upon attachment and alignment of said implant on said fractured bone said fractured bone is restored to its approximate pre-fracture length, said fastener receiving openings being generally adapted to receive screws, wires, cables or other fastening means therein.

26. The implant as claimed in claim 1 wherein said implant is sufficiently pliable to be contoured to the shape of the long bone to be repaired, sufficiently strong to provide support for weight bearing bones during mobility and sufficiently long to span the fracture zone and be secured at the extremities of the long bone to which it is to be attached.

27. An implant according to claim 1 wherein said implant is made of an inert material which is capable of providing a stable means of support to fractured long bones during the healing process and wherein said inert material is selected from the group consisting of stainless steel, titanium or other suitable inert material and wherein said solid cylindrical rod is designed to be sufficiently strong to provide support to said fractured bone and withstand stress bending on weight bearing long bones.

* * * * *